(12) United States Patent
Sood et al.

(10) Patent No.: US 9,984,199 B2
(45) Date of Patent: May 29, 2018

(54) METHOD AND SYSTEM FOR CLASSIFICATION AND QUANTITATIVE ANALYSIS OF CELL TYPES IN MICROSCOPY IMAGES

(71) Applicant: GE Healthcare Bio-Sciences Corp., Piscataway, NJ (US)

(72) Inventors: Anup Sood, Clifton Park, NY (US); Fiona Ginty, Niskayuna, NY (US); Nicole Evelyn LaPlante, Niskayuna, NY (US); Christopher James Sevinsky, Watervliet, NY (US); Qing Li, Niskayuna, NY (US); Alberto Santamaria-Pang, Niskayuna, NY (US); Raghav Krishna Padmanabhan, Aliso Viejo, CA (US)

(73) Assignee: GE HEALTHCARE BIO-SCIENCES CORP., Piscataway, NJ (US)

( * ) Notice: Subject to any disclaimer, the term of this patent is extended or adjusted under 35 U.S.C. 154(b) by 290 days.

(21) Appl. No.: 14/718,558

(22) Filed: May 21, 2015

(65) Prior Publication Data

US 2016/0341731 A1    Nov. 24, 2016

(51) Int. Cl.
  *G01N 33/574*  (2006.01)
  *G06F 19/18*  (2011.01)
  *G06F 19/24*  (2011.01)

(52) U.S. Cl.
  CPC ............ *G06F 19/18* (2013.01); *G06F 19/24* (2013.01)

(58) Field of Classification Search
  CPC ..................... G06F 19/18; G06F 19/24
  See application file for complete search history.

(56) References Cited

U.S. PATENT DOCUMENTS

| | | | |
|---|---|---|---|
| 8,285,719 B1* | 10/2012 | Long | G06F 17/30598 707/737 |
| 2003/0147558 A1* | 8/2003 | Loui | G06K 9/00624 382/225 |
| 2007/0003922 A1* | 1/2007 | Amaral | G01N 33/56972 435/4 |
| 2011/0177966 A1* | 7/2011 | Le Loet | C12Q 1/6883 506/9 |
| 2013/0290225 A1* | 10/2013 | Kamath | G06K 9/00127 706/12 |
| 2015/0011401 A1* | 1/2015 | Davicioni | C12N 15/111 506/2 |
| 2015/0118247 A1* | 4/2015 | Hotson | C07K 16/2818 424/142.1 |
| 2016/0341745 A1* | 11/2016 | Commissiong | G01N 33/6896 |

* cited by examiner

*Primary Examiner* — Sean Conner
*Assistant Examiner* — Pinalben Patel
(74) *Attorney, Agent, or Firm* — Wood IP LLC

(57) ABSTRACT

The disclosed embodiments are directed to a method for accurately counting and characterizing multiple cell phenotypes and sub-phenotypes within cell populations simultaneously by exploiting biomarker co-expression levels within cells of different phenotypes in the same tissue sample. The disclosed embodiments are also directed to a simple intuitive interface enabling medical staff (e.g., pathologists, biologists) to annotate and evaluate different cell phenotypes used in the algorithm and the presented through the interface.

34 Claims, 8 Drawing Sheets
(5 of 8 Drawing Sheet(s) Filed in Color)

METHOD AND SYSTEM FOR CLASSIFICATION AND QUANTITATIVE ANALYSIS OF CELL TYPES IN MICROSCOPY IMAGES

The file of this patent contains at least one drawing executed in color. Copies of this patent with color drawings will be provided by the United States Patent and Trademark Office upon request and payment of the necessary fee.

BACKGROUND

The tissue microenvironment is comprised of cells of distinct lineage and function. Better classification of the cellular composition and attendant phenotype of individual cells in the tissue microenvironment in healthy and disease states should advance basic, translational, and clinical research and ultimately improve human health. This is especially true in cancer. Immunotherapies are emerging as one of the success stories of treating cancer. Intense effort is also being expended in designing anti-cancer therapies targeting the elements of the tumor stroma including the vasculature, as well as other elements of the microenvironment. That the recent success of immunotherapies is limited to subsets of patients underscores the urgent need to develop new tools for in situ tissue microenvironment analysis and cell type quantification so as to facilitate the utilization of these treatments. Identifying the different numbers and kinds of cells is a critical task in characterizing the immune response in cancer tissues. However, there are multiple challenges to overcome to perform this task reliably. For example, the phenotypes are identified based on features computed from the biomarker expression on each cell. One simple way to identify cells that are positive for biomarkers would be to define numerical thresholds per biomarker. However, the biomarkers used to identify these cell types exhibit a great degree of variability in terms of their expression on cells of interest. Thus, defining thresholds to classify phenotypes might not perform efficiently in all cases. Also, due to differences in staining protocol and tissue fixation these thresholds would vary from slide to slide for each biomarker being analyzed. Thirdly, the cells being analyzed are two dimensional projections of three dimensional objects and this, in certain cases, affects the computation of features. The classification methods should be robust to these potential causes of variability.

The final images being analyzed also contain several artifacts which include dust particles, bubbles, tissue folding, fragments etc. which may be due to poor tissue quality as well as sample preparation. These artifacts can be misclassified as cells and can increase the false positive rate. The methods being used to process these images should take into account the incidence of artifacts and should discard them from analysis.

Large scale discovery studies involve analysis of hundreds of slides which can result in the analysis of millions of cells. Classifying millions of cells by training an algorithm requires efficient and scalable methods of training and classification. Since the number of cells identified in a large study can run into the millions, there is a need to classify cells types efficiently. One method described in patent publication 2014/0199704, published Jul. 17, 2014 uses quantile based thresholding methods to identify and classify immune cells. The present invention is directed to an improved method of letting the algorithm guide the user to select the slides from which the training data needs to be created and use the manually annotated training data to build models applicable to those or similar slides. The slide selection is done via unsupervised analysis of slide data and clustering them into groups that are similar to each other.

SUMMARY

The disclosed embodiments are directed to a method for accurately counting and characterizing multiple cell types, phenotypes and sub-phenotypes within cell populations simultaneously by exploiting biomarker co-expression features within cells of different phenotypes in the same tissue sample.

The disclosed embodiments are also directed to a method of quantifying cells of a particular cell type in a sample using a bio-semantic model comprising:

collecting of images from a plurality of biomarkers from different fields of views, the plurality of biomarker images comprising at least images of two biomarkers present in the said cell type, wherein at least one is cell-type specific, and at least one segmented image per field of view at the single cell level;

annotating a sub-set of cells for being positive or negative for a particular target on the representative images of the signal distribution of the target; and building a classification algorithm applying a partially supervised multi-class, multi-label hierarchical cell classification based on a bio-semantic model to determine quantity of a plurality of the cell-type specific cells in the biological sample.

The disclosed embodiments are also directed to a method wherein the segmented images are generated by applying a plurality of biomarkers to a biological sample; and acquiring image data of the biological sample at multiple fields of view representative of the respective plurality of biomarkers bound to a respective plurality of targets in the biological sample, wherein at least one of the plurality of biomarkers comprises an epithelium biomarker, a membrane biomarker, a cytoplasm biomarker, or a nuclear biomarker specific for a cell nucleus The disclosed embodiments also relate to embodiments of the preceding methods comprising multiple samples including a step of grouping/clustering slides into superslides based on threshold similarity of immune marker metrics between slides.

The disclosed embodiments also relate to an embodiment of the preceding methods wherein the representative images are selected by ranking the images by an intensity feature for each immune biomarker according to each phenotype metric.

The disclosed embodiments also relate to an embodiment of the preceding methods wherein the biomarkers are applied in a sequential manner, wherein after each biomarker (or set of biomarkers) application, images are acquired prior to removing the signal and application of another biomarker (or set of biomarkers).

Another embodiment of the present disclosure is directed to a method of quantifying cells of a particular cell type in a sample using a bio-semantic model comprising:

collecting of images from a plurality of biomarkers from different fields of views, the plurality of biomarker images comprising at least images of two cell-type specific biomarkers which are mutually exclusive in their expression in two different cell types, and at least one segmented image per field of view at the single cell level;

annotating a sub-set of cells for being positive or negative for a particular target on the representative images of the signal distribution of the target; and building a classification algorithm applying a partially supervised multi-class, multi-label hierarchical cell classification based on a bio-semantic model to determine quantity of a plurality of the cell-type specific cells in the biological sample.

Yet another embodiment of the present disclosure is directed to a method for quantifying infiltration of immune cell populations in a tumor microenvironment comprising:

arranging a collection of slides containing sections of a biological sample;

applying a plurality of biomarkers to the biological sample;

acquiring image data of the biological sample slides representative of the respective plurality of biomarkers bound to a respective plurality of targets in the biological sample, wherein at least one of the plurality of biomarkers comprises an epithelium biomarker, a membrane biomarker, a cytoplasm biomarker, or a nuclear biomarker specific for a cell nucleus and wherein at least one of the plurality of biomarkers comprises a biomarker specific for a cell type specific marker;

segmenting individual cells in the biological sample of the slide, wherein identifying individual cells uses image data representative of the epithelium biomarker, the membrane biomarker, the cytoplasm biomarker, or the nuclear biomarker;

grouping/clustering slides into superslides based on threshold similarity of cell type marker metrics between slides;

ranking superslide images for each cell type marker according to each phenotype metric;

annotating a subset of cells according to a bio-semantic model of cell types together with distribution of image data metrics and including distinguishing cells positive or negative for each phenotype attribute;

building a classification algorithm comprising applying a partially supervised multi-class, multi-label hierarchical cell classification based on a bio-semantic model to determine a distribution, location, and type of a plurality of cell types in the biological sample.

Another embodiment of the present disclosure is directed to a method, wherein the biological-driven descriptors (biomarkers/probes) include cytoplasmic and membrane bound proteins indicative of immune cell lineages and functional polarization states include: CD20+, CD3+, CD4+, CD8+, CD19, CD79, FoxP3+, CD11c, CD123, CD56, CD16, CD14, CD33, CD68, CCL10, CCL11, CCL5, CCL8, CCL9, CCL2, CCL3, CCL4, CXCL9, CXCL10, CXCL11, CD86, CD80, IL-1R I, MHC II, TNF-α, IL-1, IL-6, IL-12, IL-23, TLR2, TLR4, iNOS; Scavenger receptor, Mannose Receptor, CD163, Arginase 1, IL-10, TGF-β, IL-1ra, CCL24, CCL17, CCL22, CCL1, IL-1, IL-6, IL-10, MHC II, TNF-α, IL-10, TGF-β, IL-4, IL-13, CCR2, TLR1, and TLR8. Other markers include those described in the "CD Marker Handbook Human and Mouse," BD Biosciences, https://www.bdbiosciences.com/documents/cd_marker_handbook.pdf, BD Biosciences, 2350 Qume Drive, San Jose, Calif. 95131, bdbiosciences.com (2010).

Superslides as used herein refer to groupings of similar slides into a larger group such that all of the data in each of the slides is merged into one group.

Another embodiment of the present disclosure is directed to a method, wherein the biological-driven descriptors include nuclear, cytoplasmic and membrane bound proteins indicative of specific cell types.

Another embodiment of the present disclosure is directed to a method, wherein the biological-driven descriptors include nuclear, cytoplasmic and membrane bound proteins indicative of functional polarization states or phenotypes.

Another embodiment of the present disclosure is directed to a method wherein grouping/clustering slides whose similarity is above a threshold score is performed by computing a similarity image data score representative of the plurality of cell type marker metrics including intensity metrics, morphology metrics, and shape based metrics for each slide.

Another embodiment of the present disclosure is directed to a method, wherein said intensity metrics include mean, median, standard deviation, and maximum intensity value. Texture based features such as Law's metrics, Co-occurrence matrix based (Singh, Maneesha, and Sameer Singh, "Spatial texture analysis: a comparative study", Proceedings 16th International Conference on Pattern Recognition, Vol. 1. IEEE, 2002.), wavelet-based metrics such as Lipschitz regularity (see Sebe, Nicu, and Michael S. Lew. "Wavelet based texture classification." Pattern Recognition, 2000. Proceedings. 15th International Conference on. Vol. 3. IEEE, 2000.) and others.

Another embodiment of the present disclosure is directed to a method, wherein the morphology metrics include but aren't limited to area, perimeter, minor axis, and major axis.

Another embodiment of the present disclosure is directed to a method wherein the shape based metric include shape descriptors and morphology descriptors (see Santamaria-Pang, Alberto, Yuchi Huang, and Jens Rittscher. "Cell segmentation and classification via unsupervised shape ranking." Biomedical Imaging (ISBI), 2013 IEEE 10th International Symposium on. IEEE, 2013.).

Another embodiment of the present disclosure is directed to a method, wherein grouping/clustering slides based on similarity of cell type markers comprises constructing a similarity metric such as Jensen-Shannon divergence and unsupervised hierarchical clustering algorithms between all slides and ranking those similarity scores.

Another embodiment of the present disclosure is directed to a method, wherein said ranking slide images for each cell type marker is performed according to each phenotype metric.

Another embodiment of the present disclosure is directed to a method, wherein annotating a subset of cells according to a bio-semantic model of cell types together with distribution of image data metrics is performed on each similarity grouping and involves annotating cells throughout the intensity spectrum in accordance with semantic rules.

Another embodiment of the present disclosure is directed to a method, wherein annotating a subset of cells together with distribution of image data metrics is performed on each similarity grouping and involves annotating cells throughout the intensity feature spectrum, e.g if the slides are grouped by similarity in mean signal intensity per cell, then the cells may be annotated using the whole spectrum of mean signal intensities present in that group.

Another embodiment of the present disclosure is directed to a method, wherein a cell shape and morphology probability threshold score derived from the classification algorithm and the bio-semantic model applied to the specific cell type and tissue architecture excludes segmentation artifacts.

Another embodiment of the present disclosure is directed to a system for assessing a biological sample from a patient comprising:

a memory storing instructions for:

collecting of images from a plurality of biomarkers from different fields of views, the plurality of biomarker images comprising at least images of two biomarkers present in the said cell type, wherein at least one is cell-type specific, and at least one segmented image per field of view at the single cell level;

annotating a sub-set of cells for being positive or negative for a particular target on the representative images of the signal distribution of the target; and building a classification algorithm applying a partially supervised multi-class, multi-label hierarchical cell classification based on a bio-semantic model to determine quantity of a plurality of the cell-type specific cells in the biological sample.

Another embodiment of the present invention is directed to a system for assessing a biological sample from a patient comprising:

a memory storing instructions for:

arranging a collection of slides containing sections of a biological sample;

applying a plurality of biomarkers to the biological sample in a sequential manner;

acquiring image data of the biological sample slides representative of the respective plurality of biomarkers bound to a respective plurality of targets in the biological sample, wherein at least one of the plurality of biomarkers comprises an epithelium biomarker, a membrane biomarker, a cytoplasm biomarker, or nuclear biomarker specific for a cell nucleus and wherein at least one of the plurality of biomarkers comprises an biomarker specific for a cell type specific marker;

segmenting individual cells in the biological sample of multiplicity of slides, wherein identifying individual cells uses image data representative of the epithelium biomarker, the membrane biomarker, the cytoplasm biomarker, or the nuclear biomarker;

grouping/clustering slides into superslides based on threshold similarity of cell type marker metrics between slides;

ranking superslide images for each cell type marker according to each phenotype metric;

annotating a subset of cells according to a bio-semantic model of cell types together with distribution of image data metrics and including distinguishing cells positive or negative for each phenotype attribute;

building a classification algorithm comprising applying a partially supervised multi-class, multi-label hierarchical cell classification of the bio-semantic model to determine a distribution, location, and type of a plurality of cell types in the biological sample.

The aspects of the disclosed embodiments are also directed to a method of utilizing a new analytical approach for characterizing immune response in formalin-fixed paraffin embedded cancer tissue in very large cohorts wherein the analytical method utilizes a supervised clustering method for cell type classification of various cell types and subtypes. As an example, for classification and counting of T and B cells algorithm utilizes markers of cell lineage (e.g., CD markers such as CD3 for T cells and CD20 for B cells) markers and CD4 and CD8 for sub-classification of T (CD3+) cells and FOXP3 to sub-sub-classify CD4+ cells (FIG. 1).

The method allows estimating a number of statistical measurements used for correlation analysis with clinical data. Our solution involves an intelligent learning approach such that the algorithm can learn from human expertise and perform multi-phenotype cell classification in one step with intelligent data sampling.

The aspects of the disclosed embodiments are also directed to a simple intuitive interface enabling medical staff (e.g., pathologists, biologists) to annotate different cell phenotypes used in the algorithm. Such medical staff also is able to use the interface to display the images such as those depicted herein to diagnose disease and effectiveness of treatment as well as likely prognosis for the use of various therapeutic agents.

In one particular embodiment of the disclosed embodiments, a colon cancer cohort may be evaluated with the multi-phenotype classification algorithm to simultaneously classify CD3+, CD20+, CD4+, CD8+, FoxP3+ positive cells, as well as objects that are defects (with an average accuracy of 95%).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings illustrate presently preferred embodiments of the present disclosure, and together with the general description given above and the detailed description given below, serve to explain the principles of the present disclosure. As shown throughout the drawings, like reference numerals designate like or corresponding parts.

DETAILED DESCRIPTION OF THE DISCLOSED EMBODIMENTS

Figure 1:
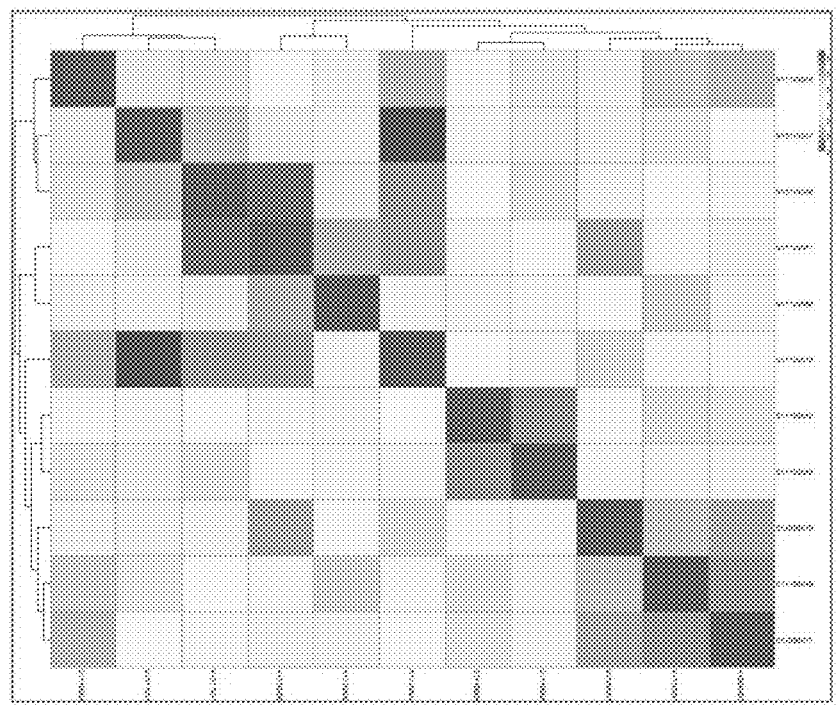
FIG. 1 refers to Slide Clustering via Jensen-Shannon Divergence. Each row and each column in the colored matrix (which is also symmetric) corresponds to a single slide. The dendrogram indicates the hierarchy obtained via hierarchical clustering. The heatmap describes the similarities between slides—Lighter colors indicate higher similarity while darker color indicates higher dissimilarity.

The tumor microenvironment (TME) is a heterotypic system of cellular and acellular elements formed de novo as a consequence of malignant tumor progression. The elements of the TME have been shown to participate directly in all aspects of cancer biology, including initiation, progression and metastatic dissemination. Several distinct cell types are found in the TME, including but not limited to malignant cancer cells, and stromal cells including different immune cell types, endothelial cells and pericytes of the blood and lymph system vasculatures, neurons, adipocytes, and fibroblasts. These cells vary in shape, size, TME distribution and function. To differentiate these cell subtypes for image analysis purposes, morphological characterization and multiple lineage markers can be required. IHC-based cell type classification is limited by the number of dyes that can be resolved on a single tissue specimen (typically 1-4).

In the case of immune cells, flow cytometry and genomic techniques such as cDNA microarrays, qPCR, and RNA-seq may suggest the presence of immune cells or the expression of genes characteristic of an immune response. With flow cytometry, the context of immune cell spatial organization and colocalization with other cell types is lost. While genomic techniques provide extensive molecular characterization, the precise cellular identities responsible for gene expression are unknown. MultiOmyx® technology allows multiple marker staining (at least 60) on the same tissue slide along with subsequent single cell analysis. These methods are compared and contrasted in Table 1. The present inventors have now characterized a panel of greater than 20 immune cell antibodies, allowing the identification of several innate and adaptive immune cell types. These immune markers can be analyzed alone, or in combination with each other for deep phenotyping. Together with epithelial and stromal segmentation, the relative location and quantity of immune cells can be established in different regions of the tumor, enabling regional assessment of immune infiltration.

TABLE 1

Comparison of molecular profiling techniques applied to cell type analysis

| Method | Sample req. | Biomarkers/sample | Advantages | Disadvantages |
|---|---|---|---|---|
| IHC | Single tissue slide | 1 marker/slide | Well established, easy to interpret | 1 marker/slide, need for serial sections; quantitation variability (if manual) |
| cDNA Microarray | Many slides (5+), | Whole genome coverage | Whole genome coverage, semi-quantitative | Lack of spatial resolution; large amount of tissue required; technical challenges with FFPE tissues (i.e. DNA fragmentation). |
| RNA-Seq | Many slides (5+), | Whole genome coverage | Whole genome coverage, semi-quantitative | Lack of spatial resolution; large amount of tissue required; technical challenges with FFPE tissues. (i.e. RNA degradation and fragmentation) |
| qPCR | Many slides (5+), | Up to ~20/sample | Simple probe design, well established technology | Lack of spatial resolution (compound cell phenotype); amount of tissue required |
| Flow cytometry | ≥1 mm³ piece of tissue no fixative | Up to ~20/sample | Well established, compound cell phenotypes; not typically used for solid tumors. | Lack of spatial resolution; large amount of tissue required |
| MultiOmyx® | Single tissue slide | Tested up to ~60, upper limit unknown | 1 tissue section required; compound cell phenotypes; quantitative; spatial resolution maintained | Cost of reagents; time consuming |

Figure 8:
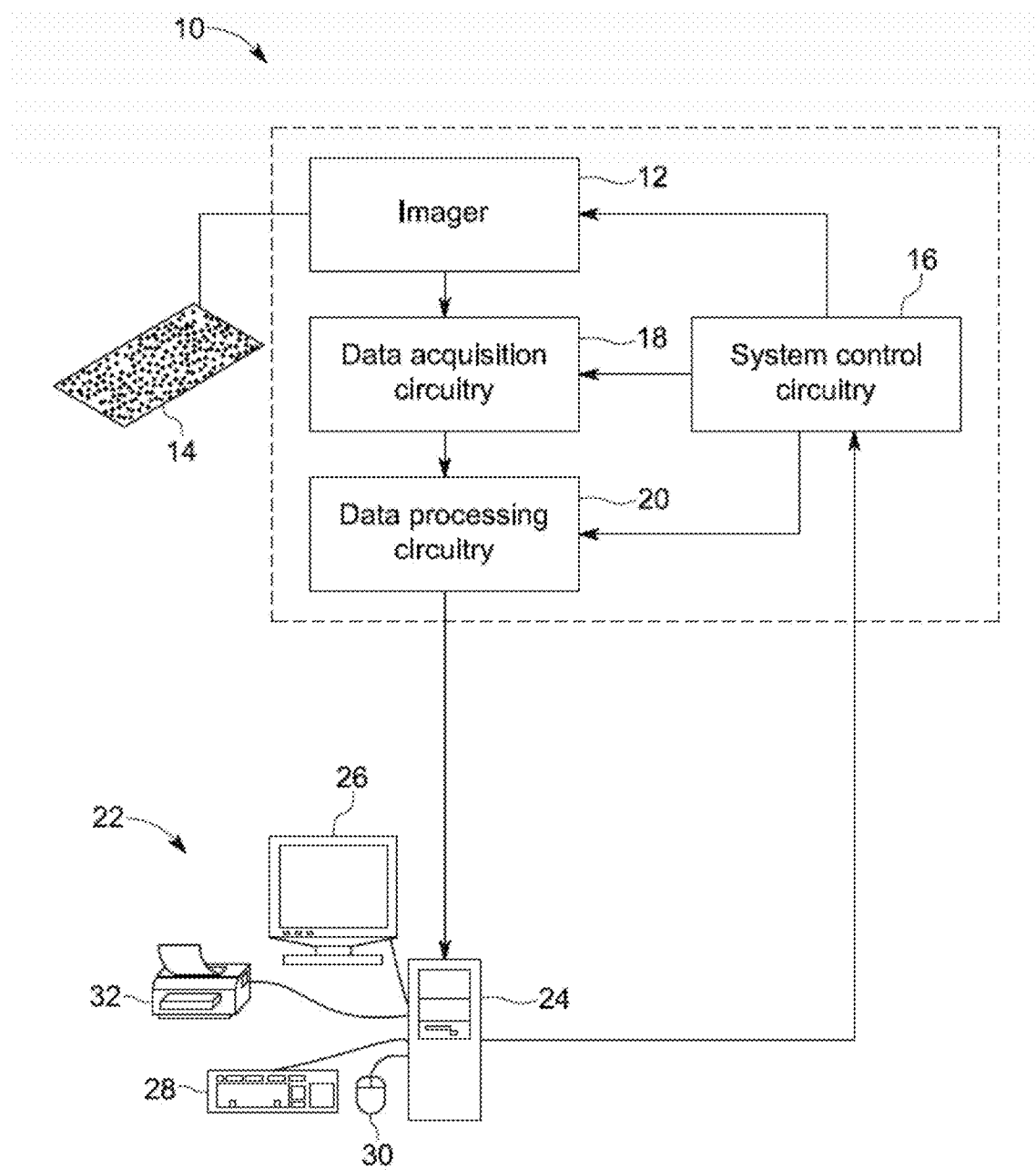
FIG. 8 is a block diagram illustrating an embodiment of a system for assessing a biological sample according to an embodiment of the present disclosure.

The present techniques provide systems and methods for image analysis. In certain embodiments, it is envisioned that the present techniques may be used in conjunction with previously acquired images, for example, digitally stored images, in retrospective studies. In other embodiments, the images may be acquired from a physical sample. In such embodiments, the present techniques may be used in conjunction with an image acquisition system. An exemplary imaging system 10 capable of operating in accordance with the present technique is depicted in FIG. 8. Generally, the imaging system 10 includes an imager 12 that detects signals and converts the signals to data that may be processed by downstream processors. The imager 12 may operate in accordance with various physical principles for creating the image data and may include a fluorescent microscope, a bright field microscope, or devices adapted for suitable imaging modalities. In general, however, the imager 12 creates image data indicative of a biological sample including a population of cells 14, shown here as being multiple samples on a tissue micro array, either in a conventional medium, such as photographic film, or in a digital medium. As used herein, the term "biological material" or "biological sample" refers to material obtained from, or located in, a biological subject, including biological tissue or fluid obtained from a subject. Such samples can be, but are not limited to, body fluid (e.g., blood, blood plasma, serum, or urine), organs, tissues, biopsies, fractions, and cells isolated from, or located in, any biological system, such as mammals. Biological samples and/or biological materials also may include sections of the biological sample including tissues (e.g., sectional portions of an organ or tissue). Biological samples may also include extracts from a biological sample, for example, an antigen from a biological fluid (e.g., blood or urine). The biological samples may be imaged as part of a slide.

The imager 12 operates under the control of system control circuitry 16. The system control circuitry 16 may include a wide range of circuits, such as illumination source control circuits, timing circuits, circuits for coordinating data acquisition in conjunction with sample movements, circuits for controlling the position of light sources and detectors, and so forth. In the present context, the system control circuitry 16 may also include computer-readable memory elements, such as magnetic, electronic, or optical storage media, for storing programs and routines executed by the system control circuitry 16 or by associated components of the system 10. The stored programs or routines may include programs or routines for performing all or part of the present technique.

Image data acquired by the imager 12 may be processed by the imager 12, for a variety of purposes, for example to convert the acquired data or signal to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired.

The data acquisition circuitry 18 may also transfer acquisition image data to data processing circuitry 20, where additional processing and analysis may be performed. Thus, the data processing circuitry 20 may perform substantial analyses of image data, including ordering, sharpening, smoothing, feature recognition, and so forth. In addition, the data processing circuitry 20 may receive data for one or more sample sources, (e.g. multiple wells of a multi-well plate). The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the computer 24 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the computer 24. The computer 24 may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. The various I/O and communication interfaces may utilize wires, lines, or suitable wireless interfaces, as appropriate or desired.

More than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images. Thus, the image processing, segmenting, and/or enhancement techniques described herein may be carried out remotely from the imaging system, as on completely separate and independent workstations that access the image data, either raw, processed or partially processed and perform the steps and functions described herein to improve the image output or to provide additional types of outputs (e.g., raw data, intensity values, cell profiles).

Figure 9:
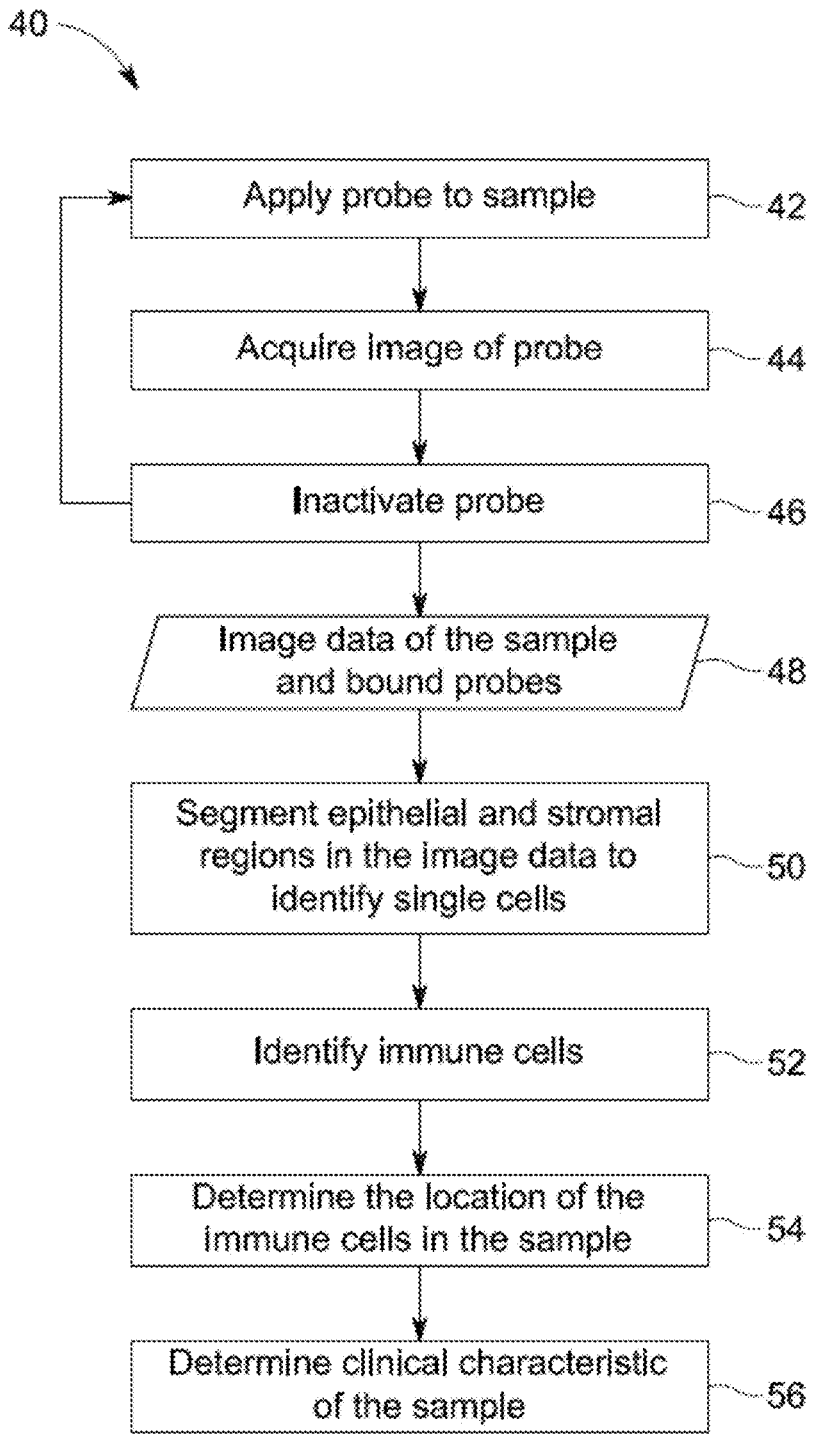
FIG. 9 is a flow diagram of a quantitative in situ biological sample characterization according to an embodiment of the present disclosure.

The computer analysis method 40 used to analyze images is shown in FIG. 9. It should be understood that the method 40 may also be used with stored images that are retrospectively analyzed. Typically, one or more images of the same sample may be obtained or provided. In step 42, the biological sample is prepared by applying a plurality of biomarkers. In one embodiment, the biomarkers are applied in a sequential manner. The biomarkers may include biomarkers for identifying tissue regions such as epithelium, endothelium or stromal regions and/or cellular regions such as the cell membrane, cytoplasm and nuclei. In such an embodiment, a mask of the stromal region may be generated, and using curvature and geometry based segmentation (step 44), the image of the compartment marker or markers is segmented. For example, the membrane and nuclear regions of a given tumor region may be demarcated. The cytoplasm may be designated as the area between the membrane and nucleus or within the membrane space or marked by a cytoplasmic marker. Any number and type of morphological markers for segmentation may be used.

FIG. 9 is a flow diagram of one embodiment of a technique 40 for assessing a biological sample as provided herein. At step 42, one or more biomarkers is applied to the biological sample 14. The biomarker may be applied as part of a multi-molecular, multiplexing imaging technology such as the GE Healthcare MultiOmyx™ platform. For example, the biomarker may be applied and an image maybe acquired at step 44 by the imaging system 10. The image may be in the form of image data that is representative of the biomarker bound to the target of interest on the sample. Rather than use a separate slide or section to then assess a second biomarker relative to the first biomarker, e.g., via image registration techniques on the acquired images, the biomarker may be inactivated, e.g., via a chemical inactivation, at step 46 before application of a subsequent second biomarker. The method 40 then returns to step 42 for sequential biomarker application, image acquisition, and biomarker inactivation until all of the desired biomarkers have been applied. In particular embodiments, the disclosed techniques may be used in conjunction with any number of desired biomarkers, including 2, 3, 4, 5, 6, 7, 8, 9, 10 or more biomarkers per sample. Accordingly, the acquired image data 48 represents a plurality of images, and individual images within the data may be associated with a detected intensity of a particular biomarker. In one embodiment, the sequential biomarker imaging may be performed as disclosed in U.S. Pat. No. 7,629,125, which is incorporated by reference herein in its entirety for all purposes. During the sample handling, certain quality control steps may be taken to account for marker staining variability. For example, replicates may be stained. Alternatively multiple marker images may be obtained by other methods, e.g., multispectral imaging that allows ~8-10 markers to be identified simultaneously.

At step 50, the image data 48 is segmented to identify individual cells. For example, for a sample including a tumor, the sample may be segmented into epithelial and stromal regions, and individual cells within the epithelial region and the stromal region may also be identified. In a particular embodiment, the biomarkers may include biomarkers to immune markers as well as biomarkers specific for segmenting markers and morphological markers, e.g., epithelium biomarkers, membrane biomarkers, cytoplasmic biomarkers, and/or nuclear biomarkers. Accordingly, the image data 48 may include information to facilitate segmenting as well as information to identify immune cell types. The method 40 may include one or more quality control features to exclude poorly stained markers or poorly segmented spots. Further, the identification of individual cells may include quality control features such as intensity or morphological thresholds to exclude certain cells based on staining or signal quality or cell area, ellipticity, etc. Once the individual cells are identified, cells that are immune cells, or any other type of cell, may be identified using the image data 48 of the bound biomarkers specific for immune cell markers. For example, while a tumor cell sample may be mostly made up of epithelial cells, there may be some immune cells that have been recruited to the area. Based on the type of tumor and the stage of progress, certain immune cells may infiltrate the epithelial regions of the tumor. Accordingly, by determining the location of the immune cells at step 54 (e.g. epithelial vs. stromal), along with the specific types of cells in the sample at step 52 (e.g., B cell, T cell, neutrophils, macrophages) as well as the relative numbers of immune cells of each type, the method 40 may determine a clinical characteristic of the sample at step 56.

The method 40 may also provide an output related to the clinical characteristic, for example via a display associated with the system 10 or stored in a memory of the system 10. The output may include one or more of a histogram, boxplot, density plot, violin plots, or numerical values corresponding to such plots. In one embodiment, the output may be an immune profile of the sample. The immune profile may include a total number of all immune cells in the sample and/or in the epithelial and stromal regions, a total number of each type of immune cell in the sample and/or in the epithelial and stromal regions, or a histogram of the immune cell types in the sample and/or in the epithelial and stromal regions. Further, for each type of immune cell that includes subtypes (e.g., N1 and N2 cells), the immune profile may also include distribution and location information for immune cell subtypes. In addition to identification of immune cells as being stromal or epithelial, the present techniques may also assess location relative to a tumor edge or infiltration into the tumor. Such assessment may be made using detected borders or other features via appropriate segmentation techniques. In one embodiment, the output may be a single marker expression average for epithelial, stromal, and whole image regions. The output may also include metrics such as skewness, a standard deviation, or coefficient of variation of the marker distribution. In another embodiment, the output may also include a percentage of positive cells in stromal, epithelial, and whole image regions that may also include additions of manual data. For example, once the image is segmented to identify cells and to identify marker distribution, an end user may then perform a manual quality check and add or remove cells. As mentioned herein below the similarity method can be used to reject artifacts.

In one embodiment, the technique may be used to assess an unknown clinical condition by comparing the immune profile of a biological condition to one or more reference profiles of known clinical conditions. The reference profiles may be stored in the memory of the system 10. In such an example, the immune profile may be used for providing a diagnosis. In another embodiment, the immune profile may be used to determine if a therapy is working. For example, certain therapies may be designed to recruit immune cells to tumor tissues, e.g., T cell therapy. Accordingly, immune profiles taken before and after treatment may be used to determine if the therapy is working. In another embodiment, the immune profile may be used to assess if a particular type of therapy is likely to be successful.

Further, the immune profile may also provide information on linked markers to identify particular clinical conditions. For example, certain markers may be co-localized in particular disease states. In addition, certain markers may be assessed in groups for quality or confidence metrics. In one embodiment, a cell type may be identified by multiple marker profiles using clustering.

The plasticity and heterogeneity of the cancer immune response has been implicated in disease prognosis. Many cells of the immune system have been shown to undergo functional polarization. Depending on local molecular cues, including the level of specific chemokines, cytokines and growth factors, many cells of the adaptive and innate immune system adopt cell killing or immunosuppressive functions. Extensive evidence has linked the immunosuppressive phenotypes of macrophages and T-lymphocytes with aggressive tumor biology in model systems and adverse clinical outcomes in human disease. Elevated expression of transforming growth factor-$\beta$ (TGF $\beta$) has been shown to be one of the main factors promoting the immunosuppressive polarization of immune cells. Other factors also contribute to the functional orientation of the immune cells in the TME. While emerging data suggest similar functional polarization of many immune cell types, recent studies of macrophage and T-lymphocyte polarization best illustrate these phenomena and are reviewed below.

Tumor Associated Macrophages (TAMs)

Macrophages are phagocytic cells with broad functions in innate and adaptive immunity as well as tissue homeostasis and wound healing. Importantly, tumor associated macrophages (TAMs) exhibit distinct functional polarization states, termed classical, or M1, and alternative, or M2. These phenotypes are observed in a variety of normal and pathological physiological processes. The M2 phenotype has been further subdivided into three classes (A,B,C), reflecting the observation of heterogeneous and context-dependent alternative activation states of macrophages. In cancers, classically activated TAMs (M1) engage in cytotoxic functions, and are associated with anticancer phenomena. Alternatively activated TAMs (M2) are associated with tumor promotion through a variety of mechanisms that include hallmark characteristics of wound healing and immune tolerance. Several candidate markers of M1 and M2 phenotypes have been advanced. The proposed markers are numerous, and are summarized in Table 2 and reviewed in N.-B. Hao, M.-H. Lü, Y.-H. Fan, Y.-L. Cao, Z.-R. Zhang, and S.-M. Yang, "Macrophages in Tumor Microenvironments and the Progression of Tumors," J. Immunol. Res., vol. 2012, p. e948098, June 2012.

The phenotypic M1/M2 dichotomy is thought to be influenced by the local TME, wherein the production of cytokines and growth factors influences the polarization of TAM phenotype. The complex nature of the stimuli responsible for macrophage polarization have been reviewed elsewhere, but general characteristics mirror Th1 and Th2 responses associated with adaptive immunity, wherein TAM polarization is mediated by classical chemokine and cytokine stimuli. Interferon Gamma (IFNγ), bacterial lipopolysaccharide (LPS) and Tumor Necrosis Factor Alpha (TNFα) are associated with M1 polarization, while Interleukin 4 (IL4), IL13 and IL10 are associated with M2 polarization. Reciprocally, M1 and M2 macrophages act through paracrine signaling to influence the TME. Through the production of signaling molecules, TAMs modulate tumor cell proliferation and motility, angiogenesis, and the state of the adaptive immune response, reflecting the highly coordinated nature of the various elements of the TME. Despite superficial simplicity of the above TAM polarization dichotomy and observations of prognostic relationships between TAMs and patient outcomes, the precise nature of TAM function in the TME is still an active area of inquiry. Establishing the disposition of the TAM population using techniques such as MultiOmyx® in context with other elements of the TME will illuminate the complex interplay of cells in the heterotypic tumor.

TABLE 2

Markers of M1 and M2 macrophage polarization.

| | |
|---|---|
| M1 TAM | CCL10, CCL11, CCL5, CCL8, CCL9, CCL2, CCL3, CCL4, CXCL9, CXCL10, CXCL11, CD86, CD80, IL-1R I, MHC II, TNF-α, IL-1, IL-6, IL-12, IL-23, TLR2, TLR4, iNOS |
| M2 TAM | Scavenger receptor, Mannose Receptor, CD163, Arginase 1, IL-10, TGF-β, IL-1ra, CCL24, CCL17, CCL22, CCL1, IL-1, IL-6, IL-10, MHC II, TNF-α, IL-10, TGF-β, IL-4, IL-13, CCR2, TLR1, TLR8 |

T-Lymphocytes:

T-lymphocytes are a complex class of adaptive immune cells identified by the expression of proteins characteristic of their differentiation and function. At the highest level, all T-lymphocytes express CD3. Further subdivision of T-lymphocyte subtypes is characterized by the expression of either CD4 or CD8. CD8+ lymphocytes are relatively homogeneous in function, and are termed cytotoxic T-cells. Cytotoxic CD 8+ T-lymphocytes are generally associated with tumor antagonistic roles. CD4+ T-lymphocytes are a complex class of cells identified by the expression of CD4, together with one or more additional proteins characteristic of the different cell types. CD4+ T-lymphocytes include Th1, Th2, Th17 and T-regulatory (T-reg) cells, as well as other lesser characterized subtypes not discussed here. The locations and mechanisms responsible for differential T-lymphocyte differentiation are complex and have been reviewed elsewhere. T-lymphocytes have been shown to exert tumor promoting and tumor antagonistic functions. The precise nature of each cell's contribution to anti and pro-tumor functions is currently being deciphered, but some general trends are apparent. Th1 polarized cells are generally associated with tumor antagonistic functions, while Th2, Th17 and T-reg cells are often found in association with tumor-promoting functions. Increasing experimental evidence from model systems and retrospective studies of cancer prognosis continues to increase support for these concepts.

While the macrophages and T-lymphocytes immune cell types are best studied, most of the cells of the immune system have been examined in cancer biology. Similar to T-lymphocytes and macrophages, many cells types studied exhibit functional heterogeneity and have been associated with negative and/or positive patient outcomes. A non-exhaustive list of immune cell types and some of the markers proposed to identify these cells is presented in Table 2.

Immune Cells and Correlation with Cancer Prognosis

Several specific aspects of tumor immunology have been shown to be associated with differential prognosis in various cancers. These attributes have fueled the development of prognostic assays that show promise in resolving questions relating to the probability of therapeutic response and the overall likelihood of disease recurrence. Robust adaptive immune cell infiltration is linked with a favorable outcome in a variety of solid tumors. Strong evidence for this phenomenon was first obtained in ovarian cancer, followed by colorectal cancer (CRC) (see Galon et al., "Type, density, and location of immune cells within human colorectal tumors predict clinical outcome," Science, vol. 313, no. 5795, pp. 1960-1964, September 2006 and Webb et al., "Tumor-infiltrating lymphocytes expressing the tissue resident memory marker CD103 are associated with increased survival in high-grade serous ovarian cancer," Clin. Cancer Res. Off. J. Am. Assoc. Cancer Res., vol. 20, no. 2, pp. 434-444, January 2014. T-cells were counted manually in 174 ovarian cancer specimens and by computer aided image analysis in a subset of 33 patients. Increasing abundance of infiltrating CD3+ or CD8+ T-lymphocytes exhibited a strong link with favorable patient prognosis in ovarian cancer. Prognosis in patients with early-stage CRC was similarly shown to be associated with T-lymphocyte abundance. An immunoscore measure has also showed a strong correlation with prognosis in 407 colon cancer patients with stage I-IV disease. An immunoscore quantified CD3+ T-cells, CD8+ cytotoxic T-cells, Granzyme B+ T-cells and CD45RO+ memory T-cells in the tumor center and at the invasive margin and a score of zero or one was assigned at each location, yielding a score ranging from 0-4. The final algorithm combined the measurement of CD3 and CD45RO and compared subjects with a high level infiltration at the invasive margin and tumor center with those receiving a low score (4 vs. 0). A high score, reflecting high level adaptive immune cell infiltration at the tumor invasive margin and the tumor center, was associated with a favorable prognosis, while a paucity of T-lymphocyte infiltration was a negative prognostic factor. These findings were validated in an independent cohort of 602 patients using a similar scoring mechanism to quantify CD8 and CD45RO positive cells on tissue microarrays constructed to include regions corresponding to the tumor center and invasive margins. While this body of data observations support a positive prognostic association with robust immune cell infiltration, other studies have demonstrated that the presence and quantity of certain immune cell types are associated with a negative prognosis.

In breast cancer, a lack of cytotoxic T-lymphocyte infiltration in conjunction with high levels of tumor associated macrophage (TAM) infiltration has been linked with negative patient prognosis. Additional cell types including myeloid derived cells, granulocytes, natural killer cells and dendritic cells have all been implicated in cancer immunology. It remains to be seen whether this trend can be generalized or is limited to certain indications. These observations underscore an emerging theme in cancer immunology of defining the preconditions of a robust anti-tumor immune response; conversely, factors promoting tolerance of incipient malignant neoplasms and cancer promoting inflammation, immunosuppression and wound healing phenotypes can likewise be systematically evaluated. These questions may be addressed by more thorough characterization of the interplay between the intrinsic properties of the patient's immune system, the genomic characteristics of the malignant cancer cells, and the status of the local tumor immune response. The present methods will allow the comprehensive identification, enumeration and functional classification of the immune cells in individual tumors examined in the context of clinical covariates, disease outcomes and therapeutic response.

Immunotherapies:

Leveraging insights into cancer immunology, immunotherapies are exhibiting unprecedented efficacies in the clinic. These include T-lymphocyte and dendritic cell based therapies and direct inhibition of immunosuppressive mechanisms with small molecules and biological drugs. Tumor antigen targeted monoclonal antibodies are also thought to act in part through adaptive immune mediated mechanisms. In two notable immune cell therapy approaches, T-lymphocytes were harvested from the blood of the cancer patient and expanded ex vivo, followed by reintroduction in to the body to fight tumors. In one instance, termed adoptive T-cell therapy (ACT), expanded cells were reintroduced into the body together with the pro-inflammatory cytokine interleukin 2. T-lymphocytes can also be genetically engineered to express chimeric antigen receptors (CAR). The CAR extracellular domain is engineered to bind to cancer cell derived antigens, while the intracellular domain serves as a signaling platform for the activation of effector functions. Both approaches have shown promise in treating diverse cancers. Antigen presenting cells have also been used in cell therapy, and one approach, Sipuleucel-T (Provenge®), achieved FDA approval in 2010 for the treatment of castration-resistant metastatic prostate cancer. Monoclonal antibodies targeting immunosuppressive mechanisms are also yielding successes as cancer treatments. Specifically, CTLA4 and PD-1 are cell surface receptors expressed by T-lymphocytes that negatively regulate effector functions when actively engaged by ligands. Blocking these interactions is intended to reduce immunosuppression, thereby improving adaptive anti-tumor immunity. The anti CTLA-4 monoclonal antibody Ipilumumab has been approved by the FDA to treat metastatic melanomas, and several PD-1 blocking monoclonal antibodies have performed well in late stage clinical trials. Nivolumab, a PD-1 blocking monoclonal antibody from Bristol-Myers Squibb, was recently approved in Japan for unresectable melanoma. Favorable responses to PD1 or CTLA-4 blockade in other tumor types have been demonstrated, suggesting approvals in additional disease indications are imminent. The pretreatment and longitudinal status of the immune system in cancers treated with immunotherapies may be an important determinant of efficacy. To date, this condition is poorly understood, warranting characterization of cancer immunology in relationship with immunotherapy treatment response.

Image Analysis Approaches for Immune Cell Quantification:

An image segmentation method for circular-like immune cells has been reported in Xiai et al., "An Image Segmentation Method for Quasi-circular Immune Cells," in 2010 International Symposium on Intelligence Information Processing and Trusted Computing (IPTC), 2010, pp. 353-356. The method uses a global intensity threshold together with morphology to identify circular-cells. Immune cell analysis from nuclei and cytoplasm co-expressions have also been reported. Cell densities of CD45RO+ T cells were semi-quantitatively estimated using bright-field imaging and infiltration of CD45RO+ T cells has also been found to be a prognostic indicator in stage IIIB colon cancer. Different immune characteristics such as immune cell type, density, location within the tumor have been used to predict clinical outcome. Several immune score metrics have been reviewed elsewhere. The major drawback of the image analysis methods previously described is that immune cell characterization is limited by the low number of cell markers (due to methodological constraints) and the methods to characterize immune cells.

The present methods for the characterization of immune cells and immunophenotypes in situ using a sequential multiplexed immunofluorescence technology (MultiOmyx) is a powerful new technique for understanding complex expression patterns of many different proteins in intact tissues. This technology allows the quantification of relative expression levels of multiple proteins in individual cells. This enables the identification of cells of distinct types in heterogeneous tissues. Novel image analysis algorithms, cell classification methods and a workflow used to analyze immune cell markers in formalin-fixed paraffin embedded colorectal cancer tissue sections are described in detail below.

EXAMPLES

The immune classification algorithm was tested in a colorectal cancer dataset consisting of three slides with approximately 450 fields of view and performed using simultaneous multi-class, multi-label immune cell classification from the following markers: CD3, CD20, CD4, CD8, FoxP3 and simultaneous classification of artifacts. Multi-level phenotype dependency was integrated as follows: level one corresponds to the set of CD3+, CD20+, Negative cells and defect objects. Level 2 consists of a sub-set of CD3+ cells and corresponds to three classes: CD4+, CD8+ and negative class. Level 3 consists of a sub-population of CD4+ cells and corresponds to two classes: FoxP3+ and negative classes.

Tissue Segmentation

Fully automated tissue segmentation is achieved by identifying cell nuclei in the stroma and epithelium. The image analysis workflow implements a multi-channel algorithm that uses: i) DAPI marker and ii) epithelial cell type markers (e.g., antibodies targeting pan-cytokeratin or E-cadherin). The tissue segmentation workflow consists of cell nuclei segmentation, epithelial segmentation and stroma-epithelial cell nuclei classification. First, individual cell nuclei are segmented by applying a wavelet-based segmentation algorithm (see for example D. Padfield, J. Rittscher, and B. Roysam, "Coupled minimum-cost flow cell tracking for high-throughput quantitative analysis," Med. Image Anal., (15) 4, 650-668, (2011)) in the entire tissue (stroma and epithelium). Next, the epithelial tissue is detected using epithelium markers such as pan-cytokeratin or E-cadherin (minimum one epithelium marker, but multiple may be used). A super-epithelium image may be created by estimating a linear combination of the epithelium input images. Epithelial tissue may then be estimated from the super epithelial image by automatically calculating a global intensity threshold. Finally, DAPI is utilized to complete small gaps created by the epithelial markers (bottom of FIG. 2.). Once epithelial tissue has been segmented, nuclei cells are classified as stroma or nuclei cells based on the location relative to the epithelial mask.

Semi-Automated-Machine-Learning

Immune Marker Quantitation: Univariate statistical models using mean biomarker expression values) may not capture the underling biomarker distribution at the cell or tissue level.

It is well established that by combining weak features from univariate models to form multivariate models, better data discrimination is possible. The present invention extends univariate biomarker expression models to multivariate models by integrating four intensity features: i) mean, ii) standard deviation, iii) median and iv) maximum biomarker value. The use of multivariate models is intended to allow a more robust characterization of the biomarker heterogeneity within single cells.

The present methods apply probabilistic multi-class, multi-label classification algorithms based on multi-parametric models to detect immune cells. The classification workflow requires minimum user interactivity and uses multi-parametric data to build statistical models of biomarker expression. A multi-level machine learning framework groups slides based on similarity of marker expression and build supervised classification models for each group separately. A description of this workflow is described below:

Slide Level Clustering: Building a supervised machine learning model for identifying cell types requires annotation from expert users. A typical study involves classification of large number of images which can exhibit a great degree of variability. It is difficult for a single model to capture the range of variability in multiple markers and perform accurate classification of cells. The present methods cluster slides based on similarity of marker staining such that the variability within clusters is minimal. This is done via unsupervised analysis of slide data and clustering them into groups that are similar to each other based on the distribution of multiple markers at a cell level. The normalized histogram of mean marker expression for all the images in a slide is computed using all cells in the slide for a single marker at a time. This is an approximation for the probability distribution of marker expression for the slide. Jenson-Shannon divergence was used to compute similarity metrics between the slides being analyzed. Computing the Jensen-Shannon divergence between distributions of all the slides provides a distance matrix. One distance matrix for every marker included in the analysis is obtained. The overall distance matrix is the average of the distance matrices obtained for each marker. This average distance matrix was used to perform hierarchical clustering to group slides into distinct clusters (FIG. 1).

Hierarchical Clustering allows flexible grouping of features and also provides a heat-map representation of similarities within them. The algorithm constructs a dendrogram of the entities of interest using the features computed. The dendrogram is constructed bottom-up i.e., each entity of interest starts as a single cluster, and pairs of clusters are merged by moving up the hierarchy until all the entities are in a single cluster. In each iteration of the clustering, two clusters separated by the shortest distance are combined. The distance measure used in this method is complete linkage method where the distance between the clusters is measured by two elements (one in each cluster) that are farthest away from each other. The appropriate number of clusters is decided by the user using the color-coded heatmap representation.

A similar approach may be applied at the field of view level from a single or multiple slides to cluster the FOVs and build models for individual clusters of FOVs with minimum intracluster variability. The probability distribution of marker expression is computed for each individual image. The Jensen-Shannon divergence (see Majtey, A. P., P. W. Lamberti, and D. P. Prato. "Jensen-Shannon divergence as a measure of distinguishability between mixed quantum states." Physical Review A 72.5 (2005): 052310.) is then used to compute the similarity between images within slide or multiple slides and is used for clustering. The user annotations are used to train supervised classification models and these annotations are performed from slides and images identified by the clustering methods described above.

FIG. 1 depicts Slide Clustering via Jensen-Shannon Divergence. Each row and each column in the colored matrix (which is also symmetric) corresponds to a single slide. The dendrogram indicates the hierarchy obtained via hierarchical clustering. The heatmap describes the similarities between slides—lighter hues indicate higher similarity while darker hues indicate higher dissimilarity.

Figure 2:
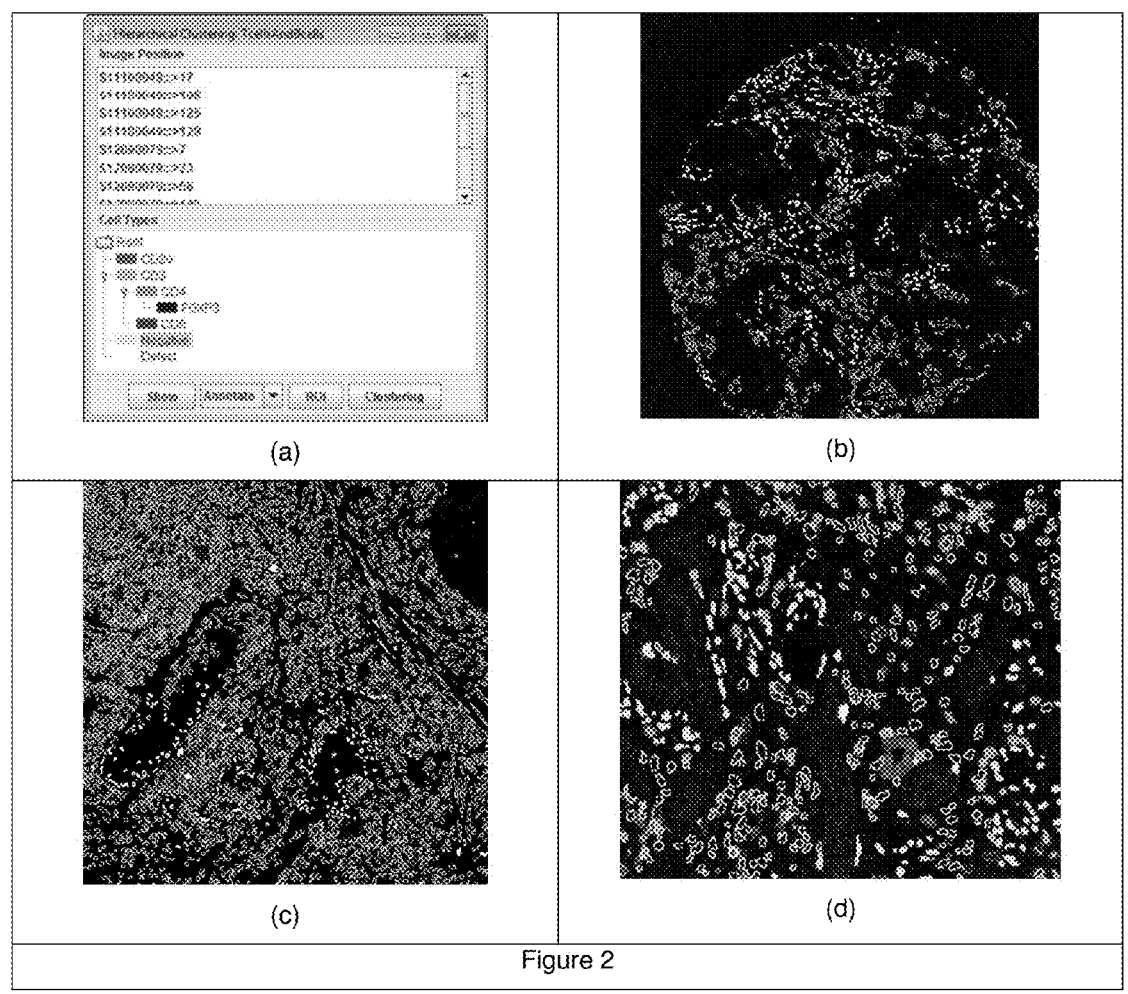
FIG. 2 refers to Cell Classification via Machine Learning. (a) Training dataset, top selected positions, and bottom cell taxonomy model. (b,c,d) Example of expert annotations in different fields of view.

User Annotations: A user provided annotations on the selected images. The cell taxonomy model is shown in FIG. 2(*a*). FIG. 2(*b,c,d*) shows overlays of the nuclei border and the cell sub-types CD20+, CD3+, CD4+, CD8+, FoxP3+, defects and negative class.

Support Vector Machines (SVM) have been used to derive a statistical model for cell classification (see Chang et. al., "LIBSVM: A Library for Support Vector Machines," ACM Trans Intell Syst Technol, vol. 2, no. 3, pp. 27:1-27:27, May 2011). The probability models are estimated from a multivariate feature vector consisting of four features: i) mean, ii) median, ii) standard deviation and iv) maximum intensity value. Additional features can be incorporated into modeling but limiting modeling to these features provides sufficient illustration of the present invention. Linear kernels are used for classification, and therefore the classification can be expressed in terms of a linear function as:

$$d(x)=W_1 * x_{mean} + W_2 * x_{median} W_3 * x_{max} + W_4 * x_{std} + C,$$

where x is the feature vector consisting of intensity measurements for the mean, median, standard deviation and maximum intensity value, and $W_i$ are the corresponding weights. Then a probability function in terms of a sigmoid function can be estimated $$P(y=1 \mid d(x)) = \frac{1}{1+e^{(a*d(x))+b)}},$$

where a, b are parameters of the sigmoid function.

Staining Performance

Figure 3:
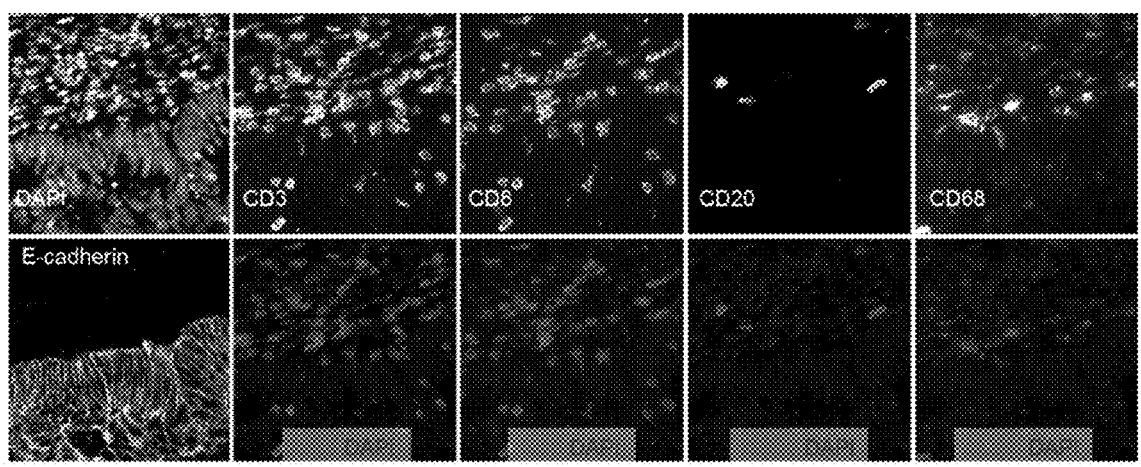
FIG. 3 refers to Lymphocyte and macrophage lineage markers staining the appropriate cells with expected localization patterns. A representative sample of an epithelial tumor-stroma interface is shown. Lymphocytes markers CD3, CD8 and CD20 exhibit membrane/cytoplasm localization. CD68 is thought to be localized to macrophage lysosomes within the cytoplasm, and exhibits amorphous cytoplasmic localization in a minority of stromal cells that are consistent with macrophage morphological characteristics.

All stains were previously validated and performed as expected in colorectal cancer specimens. Images obtained in a representative sample FOV can be seen in FIG. 3.

Epithelial and Nuclear Segmentation

Figure 4:
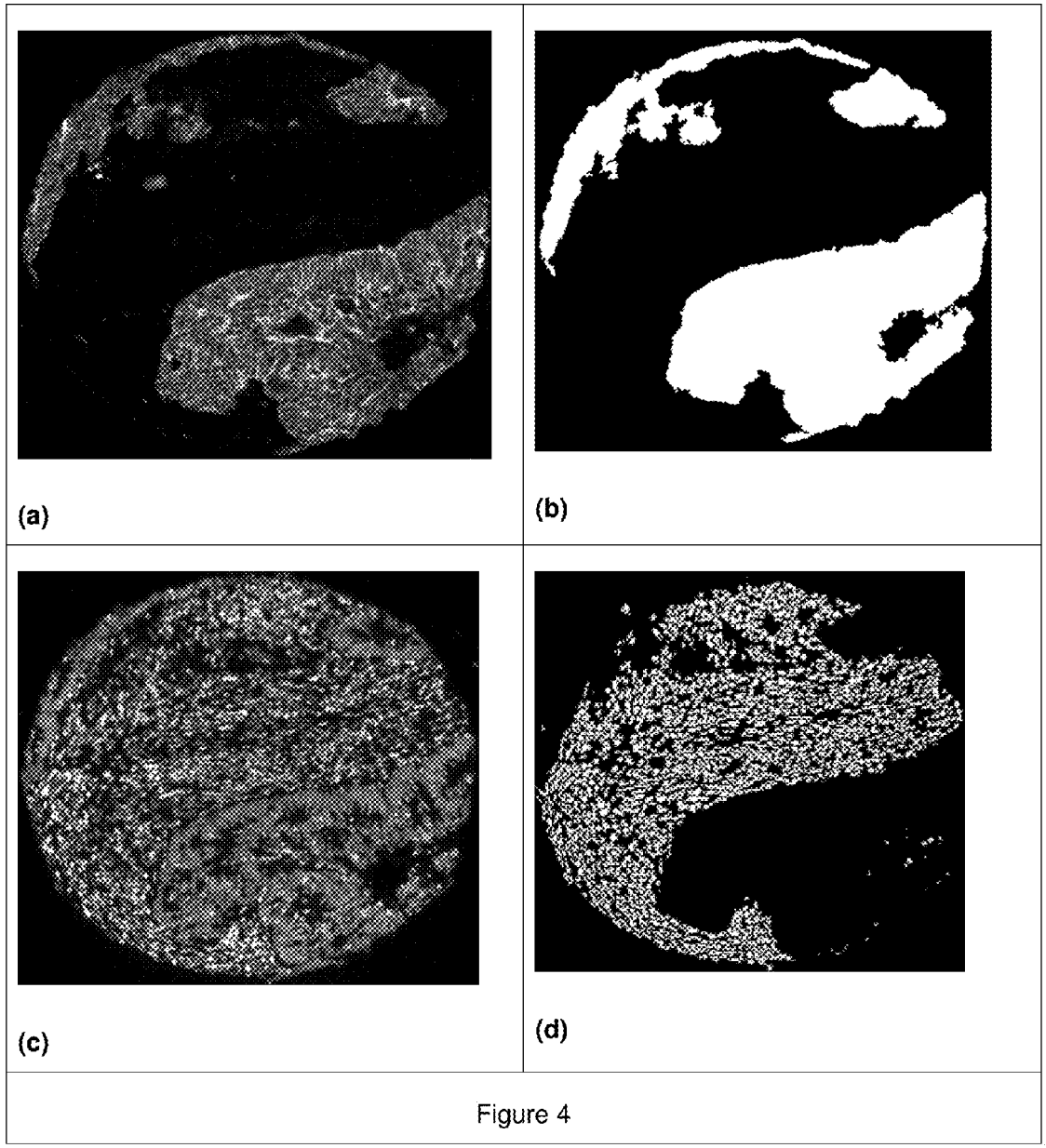
FIG. 4 refers to (a) E-Cadherin, (b) segmented epithelial tissue, (c) DAPI, (d) segmented nuclei localized in the stroma.

FIG. 4 shows segmentation markers. FIG. 4(*a,b*) shows the epithelial marker E-Cadherin and the segmented epithelial tissue. FIG. 4(*c,d*) present the DAPI marker and the segmented nuclei in the stroma respectively.

Nuclei-Based Immune Marker Quantification

Figure 5:
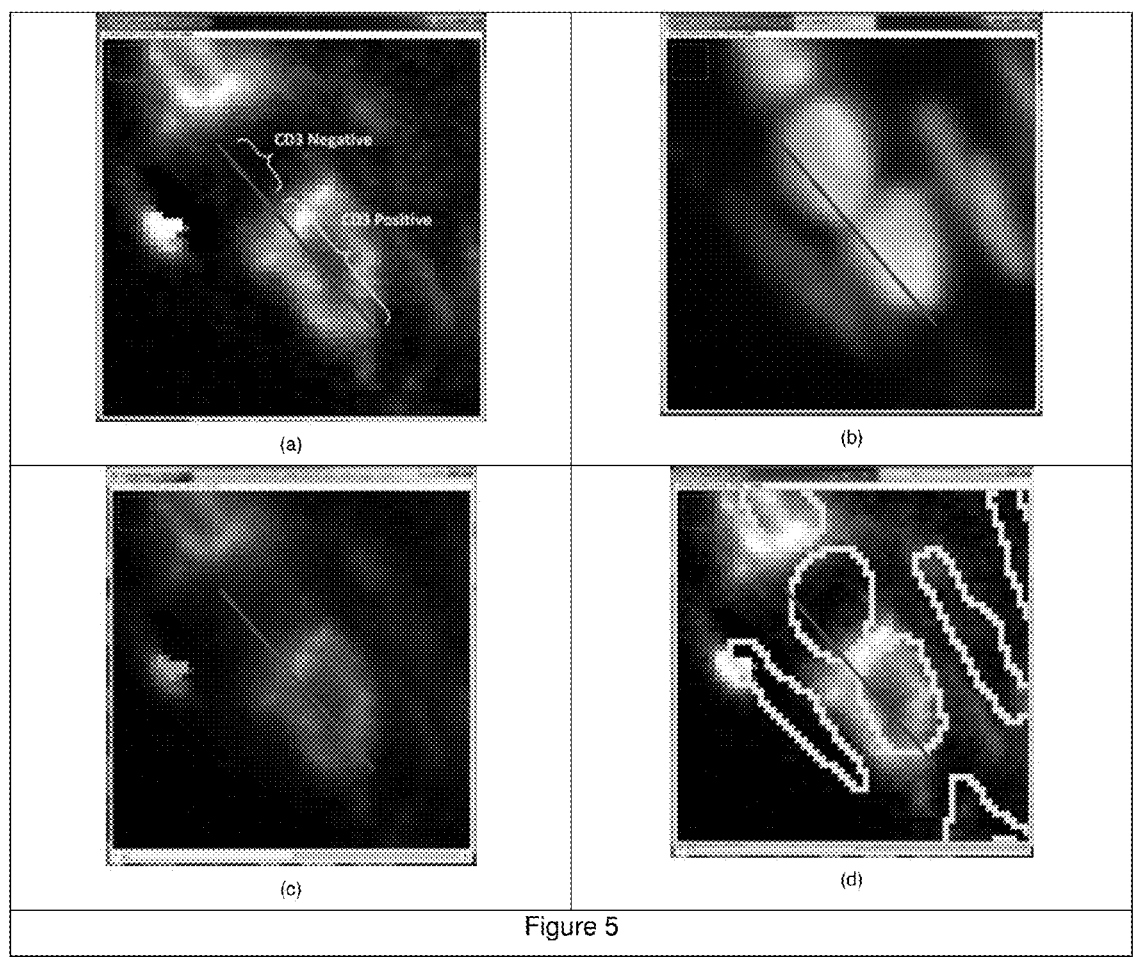
FIG. 5 depicts positive and negative CD3 expression in the nuclei. (a) Cells with positive and negative biomarker expression, (b) corresponding nuclei, (c) overlay of CD3 (green) and DAPI (blue), (d) overlay of CD3 and nuclei borders (yellow). Calibration bar in red.

FIG. 5(*a,b*) shows a representative example of CD3 staining corresponding to two adjacent cells (positive and negative) and the corresponding nuclei respectively. FIG. 5(c,d) represents overlays of CD3 staining (green) with DAPI (blue) and nuclei borders (yellow) respectively.

Figure 6:
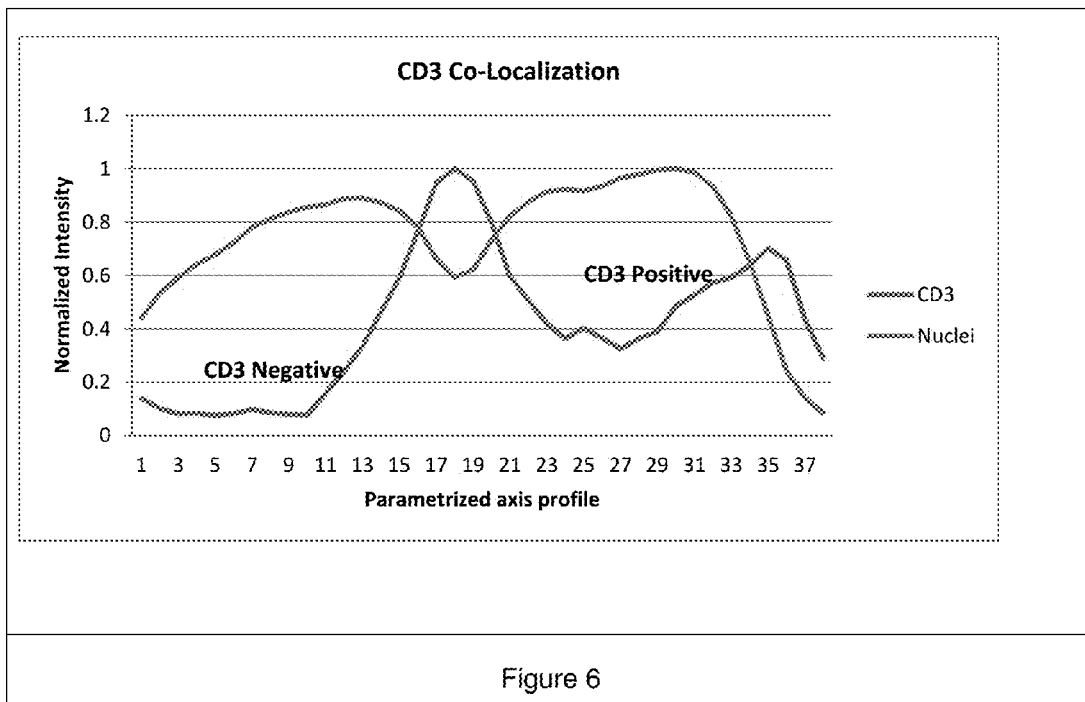
FIG. 6 refers to CD3 biomarker quantification. Biomarker quantification based on the calibration bar (red) in FIG. 6($a,b$) respectively. DAPI intensity values are in blue whereas CD3 intensity values are in green.

FIG. 6 shows the quantification of CD3 (green) and DAPI (blue) across the line profile (red) from FIG. 5(a). The line profile for CD3 (green) shows two distinct segments: a lower (valley) and upper (peak) segment corresponding to the negative and positive CD3 expression respectively. The line profile for DAPI (blue) shows similar (curved) segments for each cell nuclei. "Peak" (local maxima) for the CD3 marker corresponds to a "valley" (local minima) for the DAPI marker indicating that the maximum cytoplasmic/plasma membrane expression corresponds to a lowest DAPI expression; this is expected given that CD3 is a cytoplasmic/plasma membrane marker.

Cell Classification Accuracy

Figure 7:
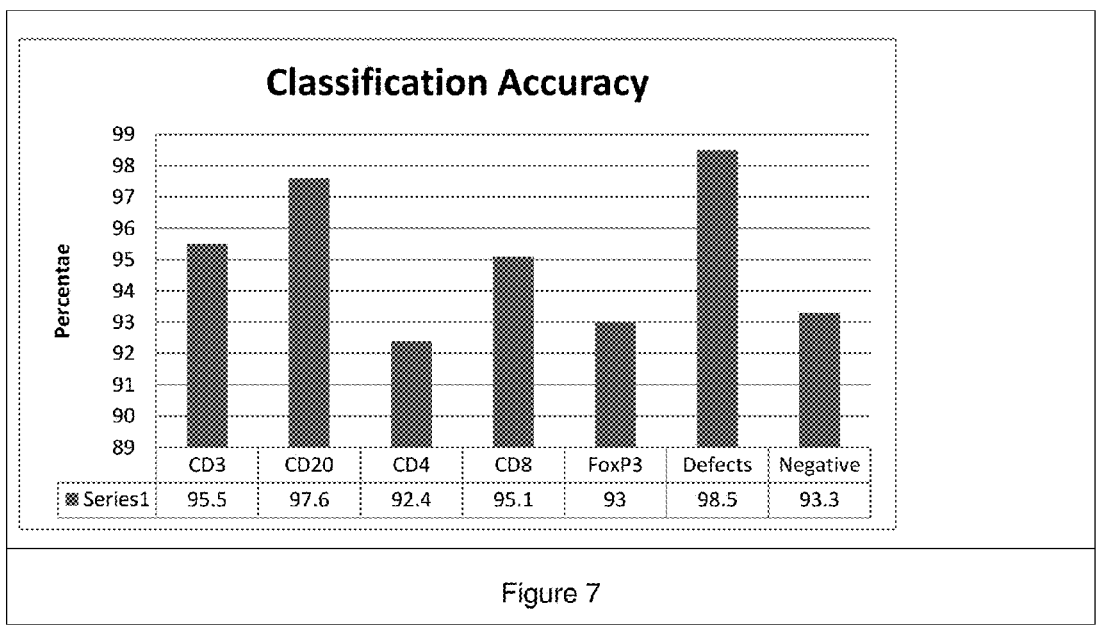
FIG. 7 illustrates cell classification accuracy.

To objectively evaluate the cell classification accuracy, a 10 stratified fold cross validation method was performed over Raykar et al., "Supervised Learning from Multiple Experts: Whom to Trust when Everyone Lies a Bit," in Proceedings of the 26th Annual International Conference on Machine Learning, New York, N.Y., USA, 2009, pp. 889-896; Kauppi et al., "Fusion of Multiple Expert Annotations and Overall Score Selection for Medical Image Diagnosis," in Image Analysis, Springer Berlin Heidelberg, 2009, pp. 760-769; He and Park, "Model Observers in Medical Imaging Research," Theranostics, vol. 3, no. 10, pp. 774-786, October 2013; Archip et al., "A Validation Framework for Brain Tumor Segmentation," Acad. Radiol., vol. 14, no. 10, pp. 1242-1251, October 2007 and report the accuracy across all the folds. FIG. 7 presents the estimated accuracy per cell phenotype from a set of 8307 cells.

Biomarker Staining and Cell-Classification

While the segmentation of the cells in the tumor stroma is based entirely on the nuclear stain DAPI, the proteins representing the different cell types classified in this report were all localized to the cytoplasm or membrane. Despite this, the methods described performed well in classifying cells, yielding greater than 90 percent accuracy in most cases relative to expert user annotations. It is notable that the classification of lymphocytes was more accurate than classification of macrophages. This is likely due to the diffuse cytoplasmic localization of the marker used to define macrophages (CD68 is localized to lysosomes) and the morphological characteristics of macrophages. In contrast, B and T lymphocytes examined here have a relatively compact cytoplasm and the cell surface markers used to define these lineages are ubiquitously expressed. Consequently, these proteins are colocalized with the nuclear masks due in part to the close physical proximity of the plasma membrane and the nucleus. In addition, the three dimensional nature of the specimens and focal depths achieved using wide-field light microscopy at 20× magnification also result in pixel level colocalization of the nuclear and non-nuclear signals.

The invention claimed is:

1. A method of quantifying cells of a particular cell type in a biological sample using a bio-semantic model comprising:
   collecting images from a plurality of biomarkers from different fields of views having signal distribution of the biomarkers, the plurality of biomarker images comprising at least images of two biomarkers present in said cell type, with at least one cell-type specific image and at least one segmented image per field of view at single cell level;
   annotating a sub-set of cells for being positive or negative for a particular biomarker on the representative images of the signal distribution of the biomarker; and
   building a classification algorithm applying a partially supervised multi-class, multi-label hierarchical cell classification based on the bio-semantic model to determine quantity of a plurality of the cell-type specific cells in the biological sample,
   wherein the biological-driven descriptors include nuclear, cytoplasmic and membrane bound proteins indicative of immune cell type and their functional polarization states include: CD20+, CD3+, CD4+, CD8+, CD19, CD79, FoxP3+, CDIIc, CD123, CD56, CD16, CD14, CD33, CD68, CCL10, CCL11, CCL5, CCL8, CCL9, CCL2, CCL3, CCL4, CXCL9, CXCL10, CXCL11, CD86, CD80, IL-1R I, MHC II, TNF-a, IL-1, IL-6, IL-12, IL-23, TLR2, TLR4, iNOS; Scavenger receptor, Mannose Receptor, CD163, Arginase 1, IL-10, TGF-(3, IL-1 ra, CCL24, CCL17, CCL22, CCL1, IL-1, IL-6, IL-10, MHC II, TNF-a, IL-10, TGF-p, IL-4, IL-13, CCR2, TLR1, and TLR8.

2. The method of claim 1, wherein said images of two biomarkers are for biomarkers present in two different cell types and are mutually exclusive to each other.

3. The method of claim 1, wherein the segmented images are generated by applying one or more biomarkers to a biological sample; and acquiring image data of the biological sample at one or more fields of view for each of the one or more biomarkers bound to the respective one or more targets in the biological sample, wherein at least one of the one or more of biomarkers comprises an epithelium biomarker, a membrane biomarker, a cytoplasm biomarker, or a nuclear biomarker specific for a cell nucleus.

4. The method of claim 1, comprising multiple samples including
   arranging a collection of slides containing sections of the biological sample;
   applying the plurality of biomarkers to the biological sample in a sequential manner;
   grouping/clustering the slides into superslides based on threshold similarity of immune marker metrics between the slides, and
   ranking the superslide for each immune marker according to each phenotype.

5. The method of claim 1, wherein the representative images are selected by ranking the images by an intensity feature for each cell-type specific marker according to each phenotype metric.

6. The method of claim 3, wherein the biomarkers are applied in a sequential manner, wherein after each biomarker application, images are acquired prior to removing the signal and application of another biomarker.

7. The method of claim 1, wherein said cell type is an immune cell.

8. The method of claim 1, wherein the biological-driven descriptors include cytoplasmic and membrane bound proteins indicative of cells derived from distinct lineages.

9. The method of claim 1, wherein the biological-driven descriptors include: CD20+, CD3+, CD4+, CD8+, and FoxP3+.

10. The method of claim 1, wherein the biological-driven descriptors include nuclear, cytoplasmic and membrane bound proteins indicative of specific cell types.

11. The method of claim 1, wherein the biological-driven descriptors include nuclear, cytoplasmic and membrane bound proteins indicative of functional polarization states.

12. The method of claim 4, wherein grouping/clustering the slides whose similarity is above a threshold score is performed by computing a similarity image data score representative of the plurality of immune markers including intensity metrics, morphology metrics, and shape based metrics for each slide.

13. The method of claim 12, wherein said intensity metrics include mean, median, standard deviation, and maximum intensity value.

14. The method of claim 12, wherein the morphology metrics include area, perimeter, minor axis, and major axis.

15. The method of claim 12, wherein the shape based metric includes shape descriptors and morphology descriptors.

16. The method of claim 12, wherein grouping/clustering the slides based on similarity of immune markers comprises constructing a similarity metric together with divergence and unsupervised hierarchical clustering algorithms applied to all slides and ranking those similarity scores.

17. The method of claim 16, wherein said ranking slide images for each immune marker is performed according to each phenotype metric.

18. The method of claim 16, wherein annotating a subset of cells according to a bio-semantic model of cell types together with distribution of image data metrics is performed on each similarity grouping and includes annotating cells throughout the intensity spectrum in accordance with bio-semantic rules.

19. The method of claim 16, wherein a cell shape and morphology probability threshold score derived from the classification algorithm and the bio-semantic model applied to the specific cell type and tissue architecture excludes segmentation artifacts from classification.

20. A method for quantifying infiltration of populations of specific cell types in a tumor or normal tissue microenvironment comprising:
arranging a collection of slides containing sections of a biological sample;
applying a plurality of biomarkers to the biological sample in a sequential manner;
acquiring image data of the biological sample slides representative of the respective plurality of biomarkers bound to a respective plurality of targets in the biological sample, wherein at least one of the plurality of biomarkers comprises an epithelium biomarker, a membrane biomarker, a cytoplasm biomarker, or nuclear biomarker specific for a cell nucleus and wherein at least one of the plurality of biomarkers comprises an immune biomarker specific for an immune marker;
segmenting individual cells in the biological sample from the multiplicity of the slides, wherein identifying individual cells uses image data representative of the epithelium biomarker, the membrane biomarker, the cytoplasm biomarker, or the nuclear biomarker;
grouping/clustering the slides into superslides based on threshold similarity of cell type marker metrics between the slides;
ranking superslide images for each cell type marker according to each phenotype metric;
annotating a subset of cells according to a bio-semantic model of cell types together with distribution of image data metrics and including distinguishing cells positive or negative for each phenotype attribute;
building a classification algorithm comprising applying a partially supervised multi-class, multi-label hierarchical cell classification of the bio-semantic model to determine a distribution, location, and type of a plurality of cells in the biological sample,
wherein grouping/clustering the slides whose similarity is above a threshold score is performed by computing a similarity image data score representative of the plurality of immune markers including intensity metrics, morphology metrics, and shape based metrics for each slide, and
wherein grouping/clustering the slides based on similarity of immune markers comprises constructing a similarity metric together with divergence and unsupervised hierarchical clustering algorithms applied to all slides and ranking those similarity scores.

21. The method of claim 20, wherein said cell type is an immune cell.

22. The method of claim 20, wherein the biological-driven descriptors include cytoplasmic and membrane bound proteins indicative of cells derived from distinct lineages.

23. The method of claim 20, wherein the biological-driven descriptors include nuclear, cytoplasmic and membrane bound proteins indicative of immune cell type and their functional polarization states include: CD20+, CD3+, CD4+, CD8+, CD19, CD79, FoxP3+, CDIIc, CD123, CD56, CD16, CD14, CD33, CD68, CCL10, CCL11, CCL5, CCL8, CCL9, CCL2, CCL3, CCL4, CXCL9, CXCL10, CXCL11, CD86, CD80, IL-1R I, MHC II, TNF-a, IL-1, IL-6, IL-12, IL-23, TLR2, TLR4, iNOS; Scavenger receptor, Mannose Receptor, CD163, Arginase 1, IL-10, TGF-(3, IL-1 ra, CCL24, CCL17, CCL22, CCL1, IL-1, IL-6, IL-10, MHC II, TNF-a, IL-10, TGF-p, IL-4, IL-13, CCR2, TLR1, and TLR8.

24. The method of claim 20, wherein the biological-driven descriptors include nuclear, cytoplasmic and membrane bound proteins indicative of specific cell types.

25. The method of claim 20, wherein the biological-driven descriptors include nuclear, cytoplasmic and membrane bound proteins indicative of functional polarization states.

26. The method of claim 20, wherein the biological-driven descriptors include: CD20+, CD3+, CD4+, CD8+, and FoxP3+.

27. The method of claim 20, wherein said intensity metrics include mean, median, standard deviation, and maximum intensity value.

28. The method of claim 20, wherein the morphology metrics include area, perimeter, minor axis, and major axis.

29. The method of claim 20, wherein the shape based metric includes shape descriptors and morphology descriptors.

30. The method of claim 20, wherein said ranking slide images for each immune marker is performed according to each phenotype metric.

31. The method of claim 20, wherein annotating a subset of cells according to a bio-semantic model of cell types together with distribution of image data metrics is performed on each similarity grouping and includes annotating cells throughout the intensity spectrum in accordance with bio-semantic rules.

32. The method of claim 20, wherein a cell shape and morphology probability threshold score derived from the classification algorithm and the bio-semantic model applied to the specific cell type and tissue architecture excludes segmentation artifacts from classification.

33. A system for assessing a biological sample from a patient comprising a memory that stores instructions for:
arranging a collection of slides containing sections of a biological sample;

applying a plurality of biomarkers to the biological sample in a sequential manner;

acquiring image data of the biological sample slides representative of the respective plurality of biomarkers bound to a respective plurality of targets in the biological sample, wherein at least one of the plurality of biomarkers comprises an epithelium biomarker, a membrane biomarker, a cytoplasm biomarker, or nuclear biomarker specific for a cell nucleus and wherein at least one of the plurality of biomarkers comprises an immune biomarker specific for an immune marker;

segmenting individual cells in the biological sample of multiplicity of the slides, wherein identifying individual cells uses image data representative of the epithelium biomarker, the membrane biomarker, the cytoplasm biomarker, or the nuclear biomarker;

grouping/clustering the slides into superslides based on threshold similarity of immune marker metrics between the slides;

ranking superslide images for each immune marker according to each phenotype metric;

annotating a subset of cells according to a bio-semantic model of cell types together with distribution of image data metrics and including distinguishing cells positive or negative for each phenotype attribute;

building a classification algorithm comprising applying a partially supervised multi-class, multi-label hierarchical cell classification of the bio-semantic model to determine a distribution, location, and type of a plurality of immune cells in the biological sample, wherein the biological-driven descriptors include nuclear, cytoplasmic and membrane bound proteins indicative of immune cell type and their functional polarization states include: CD20+, CD3+, CD4+, CD8+, CD19, CD79, FoxP3+, CDIIc, CD123, CD56, CD16, CD14, CD33, CD68, CCL10, CCL11, CCL5, CCL8, CCL9, CCL2, CCL3, CCL4, CXCL9, CXCL10, CXCL11, CD86, CD80, IL-1R I, MHC II, TNF-a, IL-1, IL-6, IL-12, IL-23, TLR2, TLR4, iNOS; Scavenger receptor, Mannose Receptor, CD163, Arginase 1, IL-10, TGF-(3, IL-1 ra, CCL24, CCL17, CCL22, CCL1, IL-1, IL-6, IL-10, MHC II, TNF-a, IL-10, TGF-p, IL-4, IL-13, CCR2, TLR1, and TLR8.

34. The system of claim 33, wherein grouping/clustering the slides whose similarity is above a threshold score is performed by computing a similarity image data score representative of the plurality of immune markers including intensity metrics, morphology metrics, and shape based metrics for each slide, and grouping/clustering the slides based on similarity of immune markers comprises constructing a similarity metric together with divergence and unsupervised hierarchical clustering algorithms applied to all slides and ranking those similarity scores.

* * * * *